US005206354A

United States Patent [19]

Seddon et al.

[11] Patent Number: 5,206,354

[45] Date of Patent: Apr. 27, 1993

[54] DNA SEQUENCE ENCODING ACTIVE FRAGMENT OF FIBROBLAST GROWTH FACTOR, HBF-2

[75] Inventors: Andrew P. Seddon, Monroe; Peter Bohlen, Peekskill, both of N.Y.

[73] Assignee: American Cyanamid Company, Stamford, Conn.

[21] Appl. No.: 615,207

[22] Filed: Nov. 23, 1990

[51] Int. Cl.$^5$ .................... C12N 15/00; C12N 15/18; C12N 15/19

[52] U.S. Cl. .................................. 536/23.5; 530/324; 530/350; 530/399; 336/23.51

[58] Field of Search .................. 536/27; 530/399, 324, 530/350; 435/6

[56] References Cited

FOREIGN PATENT DOCUMENTS

| | | |
|---|---|---|
| 246753 | 11/1987 | European Pat. Off. . |
| 275204 | 7/1988 | European Pat. Off. . |
| 0281822 | 9/1988 | European Pat. Off. . |
| 320148 | 6/1989 | European Pat. Off. . |

OTHER PUBLICATIONS

Abraham, J. A. et al., *EMBO Journal,* 5(10):2523–2528, 1986.

Baldin, V. et al., *EMBO Journal,* 9(5):1511–1517, 1990 (May).

Ornitz, D. M., *Moll Cell. Biol.,* 12:240–247, 1992.

Vlodavsky, I., *TIBS,* 16:268–271, 1991.

Presta, M., *J. Cell. Physiology,* 149:512–524, 1991.

Imamura, T., *Science,* 249:1567–1570, 1990 (Sep.).

Isaachi, A., *PNAS,* 88:2628–32, 1991.

Burgess, W. H. et al., *J. Cell. Biochemistry,* 45:131–138, 1991.

Baird, A. et al., *PNAS,* 85:2324–2328, 1988 (Apr.).

Seno, M. et al., *Eur. J. Biochem.,* 188:239–45, 1990 (Mar.).

*Primary Examiner*—Robert J. Hill, Jr.
*Assistant Examiner*—Marianne Porta Allen
*Attorney, Agent, or Firm*—Estelle J. Tsevdos

[57] ABSTRACT

The present invention relates to novel fragments of basic fibroblast growth factor (bFGF). The mitogenic potency of one of these bFGF fragments, identified as HBF-2 is about 25–50 fold less than that of native bFGF but at least $10^3$–$10^4$ fold more active than that of previously reported synthetic fragments of bFGF. Therefore, the present invention provides the shortest fragment of bFGF that retains substantial biologic activity.

3 Claims, 3 Drawing Sheets

HBF-1
32.27
HBF-2
59.47
61.43
57.65
56.17
29.77
25.42
24.70
8.00
6.00
4.00
2.00
0.00
x 10^-1 VOLTS
x 10^1 MINUTES

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 129 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL:

( i v ) ANTI-SENSE:

( v ) FRAGMENT TYPE:

( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANISM:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO: 1:

```
AAG GAC CCC AAG CGG CTG TAC TGC AAA AAC GGG GGC TTC     39
Lys Asp Pro Lys Arg Leu Tyr Cys Lys Asn Gly Gly Phe
```

```
                30                              35

TTC CTG CGC ATC CAC CCC GAC GGC CGA GTT GAC GGG GTC      78
Phe Leu Arg Ile His Pro Asp Gly Arg Val Asp Gly Val
 40                   45                       50

CGG GAG AAG AGC GAC CCT CAC ATC AAG CTA CAA CTT CAA     117
Arg Glu Lys Ser Asp Pro His Ile Lys Leu Gln Leu Gln
            55                  60                  65

GCA GAA GAG AGA                                         132
Ala Glu Glu Arg
```

( 2 ) INFORMATION FOR SEQ ID NO: 2:

( i ) SEQUENCE CHARACTERISTICS:
( A ) LENGTH: 258 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL:

( i v ) ANTI-SENSE:

( v ) FRAGMENT TYPE:

( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANISM:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO: 2:

```
GGA GTT GTG TCT ATC AAA GGA GTG TGT GCT AAC CGG TAC      39
Gly Val Val Ser Ile Lys Gly Val Cys Ala Asn Arg Tyr
 70                  75                      80

CTG GCT ATG AAG GAA GAT GGA AGA TTA CTG GCT TCT AAA      78
Leu Ala Met Lys Glu Asp Gly Arg Leu Leu Ala Ser Lys
            85                  90                  95

TGT GTT ACG GAT GAG TGT TTC TTT TTT GAA CGA TTG GAA     117
Cys Val Thr Asp Glu Cys Phe Phe Phe Glu Arg Leu Glu
                100                     105
```

-continued

```
TCT AAT AAC TAC AAT ACT TAC CGG TCT AGA AAA TAC ACC    156
Ser Asn Asn Tyr Asn Thr Tyr Arg Ser Arg Lys Tyr Thr
    110                 115                 120

AGT TGG TAT GTG GCA TTG AAA CGA ACT GGG CAG TAT AAA    195
Ser Trp Tyr Val Ala Leu Lys Arg Thr Gly Gln Tyr Lys
            125                 130

CTT GGT TCC AAA ACA GGA CCT GGG CAG AAA GCT ATA CTT    234
Leu Gly Ser Lys Thr Gly Pro Gly Gln Lys Ala Ile Leu
135                 140                 145

TTT CTT CCA ATG TCT GCT AAG AGC                        258
Phe Leu Pro Met Ser Ala Lys Ser
        150
```

( 2 ) INFORMATION FOR SEQ ID NO: 3:

( i ) SEQUENCE CHARACTERISTICS:
( A ) LENGTH: 258 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL:

( i v ) ANTI-SENSE:

( v ) FRAGMENT TYPE:

( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANISM:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO: 3:

```
GGA GTT GTG TCT ATC AAA GGA GTG NNN GCT AAC CGG TAC     39
Gly Val Val Ser Ile Lys Gly Val Xaa Ala Asn Arg Tyr
 70                 75                  80

CTG GCT ATG AAG GAA GAT GGA AGA TTA CTG GCT TCT AAA     78
Leu Ala met Lys Glu Asp Gly Arg Leu Leu Ala Ser Lys
        85                  90                  95
```

-continued

```
NNN GTT ACG GAT GAG TGT TTC TTT TTT GAA CGA TTG GAA   117
Xaa Val Thr Asp Glu Cys Phe Phe Phe Glu Arg Leu Glu
                100                 105

TCT AAT AAC TAC AAT ACT TAC CGG TCT AGA AAA TAC ACC   156
Ser Asn Asn Tyr Asn Thr Tyr Arg Ser Arg Lys Tyr Thr
    110                 115                 120

AGT TGG TAT GTG GCA TTG AAA CGA ACT GGG CAG TAT AAA   195
Ser Trp Tyr Val Ala Leu Lys Arg Thr Gly Gln Tyr Lys
            125                 130

CTT GGT TCC AAA ACA GGA CCT GGG CAG AAA GCT ATA CTT   234
Leu Gly Ser Lys Thr Gly Pro Gly Gln Lys Ala Ile Leu
135                 140                 145

TTT CTT CCA ATG TCT GCT AAG AGC                       258
Phe Leu Pro Met Ser Ala Lys Ser
        150                 155
```

DNA SEQUENCE ENCODING ACTIVE FRAGMENT OF FIBROBLAST GROWTH FACTOR, HBF-2

BACKGROUND OF THE INVENTION

The present invention relates to novel active fragments of basic fibroblast growth factors (bFGF). The fibroblast growth factors (FGF) are multifunctional polypeptide mitogens which exhibit broad target-cell specificity (1). In the course of study of these factors, a number have been identified on the basis of the ability of extracts from various tissues, such as brain, pituitary and hypothalamus, to stimulate the mitosis of cultured cells. Numerous shorthand names have been applied to active factors in these extracts, including epidermal growth factor, platelet-derived growth factor, nerve growth factor, hematopoietic growth factor and fibroblast growth factor.

Fibroblast growth factor (FGF) was first described by Gospodarowicz in 1974 (2) as derived from bovine brain or pituitary tissue which was mitogenic for fibroblasts and endothelial cells. It was later noted that the primary mitogen from brain was different from that isolated from pituitary. These two factors were named acidic and basic FGF, respectively, because they had similar if not identical biological activities but differed in their isolectric points. Acidic and basic fibroblast growth factors (recently reviewed by Burgess, W. H. and Maciag (3) appear to be normal members of a family of heparin-binding growth factors that influence the general proliferation capacity of a majority of mesoderm and neuroectoderm-derived cells (4), including endothelial cells, smooth muscle cells, adrenal cortex cells, prostatic and retina epithelial cells, oligodendrocytes, astrocytes, chrondocytes, myoblasts and osteoblasts (Burgess and Maciag, cited above at page 584) (3). Although human melanocytes respond to the mitogenic influences of basic fibroblast growth factor but not acidic FGF, most avian and mammalian cell types respond to both polypeptides (ibid.) (3).

In addition to eliciting a mitogenic response that stimulates cell growth, fibroblast growth factors can stimulate a large number of cell types to respond in a non-mitogenic manner. These activities include promotion of cell migration into wound areas (chemotaxis), initiation of new blood vessel formulation (angiogenesis), modulation of nerve regeneration (neurotropism), and stimulation or suppression of specific cellular protein expression, extracellular matrix production and cell survival important in the healing process (Burgess and Maciag, cited above, pages 584 to 588) (3).

These properties, together with cell growth promoting action, provide a basis for using fibroblast growth factors in therapeutic approaches to accelerate wound healing and in prevention and therapeutic applications for thrombosis, artheriosclerosis, and the like. Thus, fibroblast growth factors have been suggested to promote the healing of tissue subjected to trauma (5), to minimize myocardium damage in heart disease and surgery (6 and 7), and to increase neuronal survival and neurite extension (8).

Complementary DNA clones encoding human acidic and human and bovine basic fibroblast growth factors have been isolated and sequenced, and the predicated amino acid sequences derived from the complementary DNAs agree with the structures determined by protein sequence analysis (summarized by Burgess and Maciag, cited above, at pages 580-581) (3). The data predict acidic fibroblast growth factor (hereafter referred to as aFGF) to have 155 amino acids (ibid) (3). The gene for basic fibroblast growth factor (hereafter referred to as bFGF) also codes for a 155 residue protein. For both aFGF and bFGF N-terminally truncated forms exist that exhibit full biologic activity, including the 146-amino acid bFGF originally isolated and sequenced (9) and a 131-amino acid form. Analysis of the structures demonstrates a 55% identity between aFGF and bFGF (Burgess and Maciag, cited above at page 581) (3).

Basic fibroblast growth factor may be extracted from mammalian tissue, but this requires several steps even when heparin-linked affinity chromatography is employed (U.S. Pat. Nos. 4,785,079 and 4,902,782 to Gospodarowicz, et al.) (10 and 11), and the 146-amino acid species is generally obtained if extraction is done in the absence of protease inhibitors (ibid., column 9, lines 29 to 32). Bovine and human basic fibroblast growth factor cDNA have been expressed in *E. coli* (12 and 13) and S. cervisiae (36). However, reported yields of product are low (15), and recombinant factors exhibit a marked tendency to undergo thiol-disulfide interchanges promoted by free thiol groups in the protein that result in the formation of disulfide scrambled species (12).

A number of basic fibroblast growth factor analogues have been suggested. Muteins of bFGF having amino or carboxyl terminal amino acids deleted, amino acids added, cysteine substituted with a neutral amino acid such as serine, or aspartic acid, arginine, glycine, serine, or valine substituted with other acids have been suggested to have enhanced stability (16). The muteins comprise two or three additions, deletions or substitutions, with substitution of serine for cysteine the most preferred substitution (16). Arakawa and Fox (17) suggested replacing at least one, and more preferably two, of the cysteines found in natural bFGF with a different amino acid residue to yield a more stable analogue (page 4, lines 44 to 47); serine was illustrated in the Examples (page 13, lines 22 to 23). Similarly, recombinant aFGFs having extraneous bond-forming cysteine replaced with serine, and oxidation-prone cysteine, methionine and trypotophan replaced with alanine, valine, leucine or isoleucine, to yield factors having enhanced or improved biological activity have also been suggested (18).

A bFGF mutein lacking 7 to 46 amino acids from the carboxyl terminus and, optionally, having amino acid replacements was suggested to have improved stability while retaining activity in Eur. Pat. Ap. Pub. No. 326,907 to Seno, et al. (page 2, line 50 to page 3, line 4) (19). Fiddes, et al, (Eur. Pat. Ap. Pub. No. 298723) (20) suggested replacing basic or positively charged residues in the heparin binding domain encompassing residues 128 to 138 with neutral or negatively charged amino acids to produce forms of FGF having reduced heparin binding ability and enhanced potency (page 5, line 45, and page 5, line 54 to page 6, line 16). Bergonzoni, et al.(21), suggested six analogues: 1) M1-bFGF, lacking residues 27 to 32; M2-bFGF, lacking residues 54 to 58; M3-bFGF, lacking residues 70 to 75; M4-bFGF, lacking residues 78 to 83; M5-bFGF, lacking residues 110 to 120; M5a-bFGF, having the position 128 lysine and the position 129 arginine replaced with glutamine residues; and M6b-bFGF, having the positions 119 and 128 lysines and the positions 118 and 129 arginines replaced by glutamine residues.

Fortunately, the affinity for heparin also provides a selective method for isolation and purification of the two forms of FGF, acidic and basic (22). FGFs are structurally labile but can be protected from inactivation by heat or low pH by association with heparin (23). Heparin-FGF complexes also are highly resistant to proteolytic degradation (24). Heparin, through a mechanism most probably related to enhanced stability of the fibroblast growth factor can potentiate the biologic properties of both acidic and basic FGF (23 and 25). FGFs lack a classical signal peptide sequence which can direct secretion of the FGF into extracellular space (26). However, considerable quantities of bFGF have been detected in and isolated from the extracellular matrix (ECM) both in vitro (27) and in vivo (28). This, therefore, raises the question of how secretion of FGF occurs and suggests the possible use of a carrier protein or proteoglycan. ECM-associated bFGF is bound to heparin sulfate (HS) proteoglycans (29 and 31) and is most likely released in a controlled manner a as FGF-HS complex (31). Thus, a current hypothesis (1) regarding the mechanism for regulation of the mitogenic activity of FGF is that FGF is sequestered in the ECM as a biologically inactive FGF-heparin sulfate proteoglycan complex. Then, ECM-bound FGF may be mobilized by specific cellular signals that activate, for example, matrix-degrading enzyme systems such as the plasminogen activation cascade (31) and heparan sulfate-specific endo-beta-D-glucuronidases (32 and 33).

As such, it seems that locating the functional domains on bFGF should involve reviewing this structure function interaction with heparin and the receptor for FGF. In fact, structure function studies with synthetic peptide fragments of bFGF suggest the existence of two functional domains, corresponding to residues 33–77 and 112–155 (The numbering for bFGF adopted here is for the 155 amino acid form as described in (26), and refers to the methionine initiation codon as position 1. Using this system the N-terminal prolyl residue of the sequenced 146 amino acid tissue derived form of bFGF corresponds to codon position 10 and is thus identified as bFGF (10-155)). Heparin and receptor-binding domains were identified by the ability of synthetic peptides related to FGF sequences to compete with bFGF for its receptor, to bind to radiolabeled heparin and to modulate the mitogenic response of FGF (34). From one of these regions containing a functional domain, an active core decapeptide (115–124) was produced. However, the peptide (115–124) had decreased affinity for heparin and biologic potency by 10-and 100-fold, respectively in comparison to peptide 112–155 (34).

Seno et al (35) provided another series of fragments to study the mitogenic and heparin-binding properties of a series of C-terminally truncated bFGF's (10-155) produced in *E. coli*. As the degree of C-terminal truncation exceeded 6 residues, affinity for heparin was markedly decreased . In the same study, two N-terminally truncated forms of bFGF, 23-155 and 50-155, were also studied. When compared to the native bFGF (10-155), bFGF (23-155) and (50-155) showed no changes in affinity for heparin but exhibited about a 2-and 50-fold decrease in mitogenic activity, respectively.

The present invention takes advantage of the specific significant interaction between heparin and bFGF to more closely define the structural domains of the growth factor that interact with heparin and the receptor for bFGF to yield a mitogenic response. The human bFGF mutant glu$^{3,5}$,ser$^{78,96}$bFGF is used for these studies for the following reasons: (a) bFGF and the mutants are equipotent; (b) the mutations of residues 3 and 5 afford considerable higher expression than the parent protein in the expression system of this invention; and (c) the mutations of cysteines at residues 78 and 96 to serines eliminates disulfide scrambling-related stability problems associated with recombinant preparations of the parent bFGF, particularly when expressed in high yield.

Proteolytic digestion of heparin sepharose-bound glu$^{3,5}$, ser$^{78,96}$ hbFGF(1-155), gives two peptide fragments that are eluted from heparin sepharose under the same conditions used to elute intact bFGF. Thus, these bFGF peptide products are heparin-binding fragments (HBF), since they are protected from proteolytic degradation by virtue of their specific interaction with heparin. The 2 peptide fragments are labeled HBF-1 (bFGF 27-69) and HBF-2 (ser$^{78,96}$ bFGF(70-155)). On heparin affinity HPLC the mixture of HBF-1 and HBF-2 is not resolved, and the two fragments coelute with a retention time identical to that of intact bFGF. It is assumed, therefore, that both fragments possess equal affinities for heparin; although the possibility that they are covalently linked or non-covalently associated to form a complex, also exists. Interestingly, HBF-1 and HBF-2 each contain a single cysteine residue corresponding to positions 34 and 101 in glu$^{3,5}$, ser$^{78,96}$ hbFGF(1-155) which are thought to be disulfide linked in the native structure (35). HBF-1 and HBF-2 are, however, efficiently resolved by RPLC in the absence of a thiol reducing agent. The fact that N-terminal sequence analysis of RPLC-purified HBFs indicates no secondary sequences argues against HBF-1 and HBF-2 being covalently linked.

Thus, HBF-1 is subjected to S-pyridylethylation (37) under non-reducing conditions, followed by N-terminal sequence analysis. This procedure gives a quantitative reaction with vinylpyridine and release of phenylhydantoin S-pyridylethyl cysteine derivative on the 8th sequencer cycle, whereas a similiary treated control, somatostatin-28 (Bachem Bioscience), in which cysteines 17 and 28 are disulfide-linked, gives no detectable phenylhydantoin- cysteine derivative at sequencer cycle 17. Thus, the data support the presence of a free sulfhydryl group in HBF-1, and by analogy, in HBF-2, as well. This implies that cysteines 34 and 101 may not be stably disulfide-linked in glu$^{3,5}$,ser-$^{76,96}$-bFGF.

Alternatively, the possibility exists of non-covalent interactions between the 2 peptides. Indirect evidence for an association between HBF-1 and -2 comes from the failure of cation exchange chromatography, despite the marked differences in net charge of the peptides and lack of disulfide linkage, to resolve the 2 fragments. Also, their behavior on both heparin and cation exchange chromatographies is indistinguishable from that of bFGF. This may imply that in the native state or when bound to heparin, regions of bFGF contained in the sequences 27-69 and 70-155 interact to yield a unique 3-dimensional structure that is required for high affinity binding to heparin. Additional support for this comes from the observation that RPLC-purified bFGF, HBF-I and HBF-2 do not retain their affinity for heparin, even after removal of HPLC solvents, but RPLC-purified bFGF and HBF-2 exhibit biologic activities.

Baird et at (34) using synthetic bFGF fragments identified 2 peptide regions, residues 33-77 and 109-129 in bFGF, that bind to heparin and exhibit weak partial against antagonist activities in biological assays. HBF-2

($ser^{78,96}$bFGF(70–155)) contains the bFGF sequence 109-129. A comparison of the potencies of FGF sequences relative to intact bFGF (Table 2) shows that the activity of HBF-2 is at least $10^3$–$10^4$ fold greater than the most active synthetic peptide known (bFGF (112–155)) (34). Recently, Seno et al (35) expressed and examined the properties of a series of C-terminally truncated versions of bFGF. These studies conclude that essential elements for receptor binding are contained in the sequence 50–109 and for heparin binding in the sequence 110–150;however, other interpretations are possible. Seno et al., also described an N-terminally truncated form of bFGF (50-155) which retains full affinity for heparin and exhibits about 2% the mitogenic activity of bFGF (10-155). Since bFGF (50-155) and HBF-2 (70-155) seem equipotent (Table 2), the FGF sequence 50–69 can thus be eliminated as contributing significantly to receptor recognition and the mitogenic response.

The present invention provides FGF fragments obtained upon proteolytic degradation of bFGF bound to heparin or heparin sepharose and include fragments which immobolize heparin sepharose analogues or heparin analogues, including ones with mitogenic activity. This invention also encompasses analogues having the cysteine residues at positions 78 and 96 replaced with other amino acids, such as, for example alanine, glycine, arginine, tryptophan, lysine, aspartic acid, glutamic acid, asparagine, glutamine, histidine, isoleucine, leucine, valine, phenylalanine, tyrosine, methionine, serine, threonine or proline. More over, the bFGF fragments of the present invention are not species specific, and include instance, bovine, ovine, porcine and others that share similar sequences homology with human bFGF.

The novel bFGF fragments of the present invention also may be prepared by recombinant protein synthesis involving preparation of DNA encoding the bFGF fragments, insertion of the DNA into a vector, expression of the vector in host cells, and isolation of the recombinant bFGF fragments thereby produced.

Because of the degeneracy of the genetic code, a variety of codon change combinations can be selected to form DNA that encodes the bFGF fragments of the present invention, so that any nucleotide deletion(s), addition(s), or point mutation(s) that result in a DNA encoding the bFGF fragments herein are encompassed by this invention. Since certain codons are more efficient for polypeptide expression in certain types of organisms, the selection of gene alterations to yield DNA material that codes for the bFGF fragments of the present invention are preferably those that yield the most efficient expression in the type of organism which is to servive as the host of the recombinant vector. Altered codon selection may also depend upon vector construction considerations.

DNA starting material which can be altered to form the DNA of the present invention may be natural (isolated from tissue), recombinant or synthetic. Thus, DNA starting material may be isolated from tissue or tissue culture, constructed from oligonucleotides using conventional methods, obtained commercially, or prepared by isolating RNA coding for bFGF from fibroblasts, using this RNA to synthesize single-stranded cDNA which can be used as a template to synthesize the corresponding double stranded DNA. As pointed out herein, proteolytic degradation of native bFGF bound to heparin or immoblized heparin can generate the fragments, as well.

Also encompassed are DNA sequences homologous or closely related to complementary DNA described herein, namely DNA sequences which hybridize, particularly under stringent conditions, to the cDNA described herein and RNA corresponding thereto.

DNA encoding the bFGF fragments of the present invention, or RNA corresponding thereto, can then be inserted into a vector, e.g., a pBR, pUC, pUB or pET series plasmid, and the recombinant vector used to transform a microbial host organisms. Host organisms may be bacterial (e.g., *E. coli* or *B. subtilis*, yeast (e.g., S. cervisiae) or mammalian (e.g., mouse fibroblast). Culture of host organisms stably transformed or transfected with such vectors under conditions facilitative or large scale expression of the exogenous, vector-borne DNA or RNA sequences and isolation of the desired polypeptides from the growth medium, cellular lysates, or cellular membrane fractions yields the desired products.

A portion (3 $\mu$g) of the 3M NaCl eluent from heparin sepharose is subject to reverse-phased HPLC on a Vydac C column as described.

Figure 2:
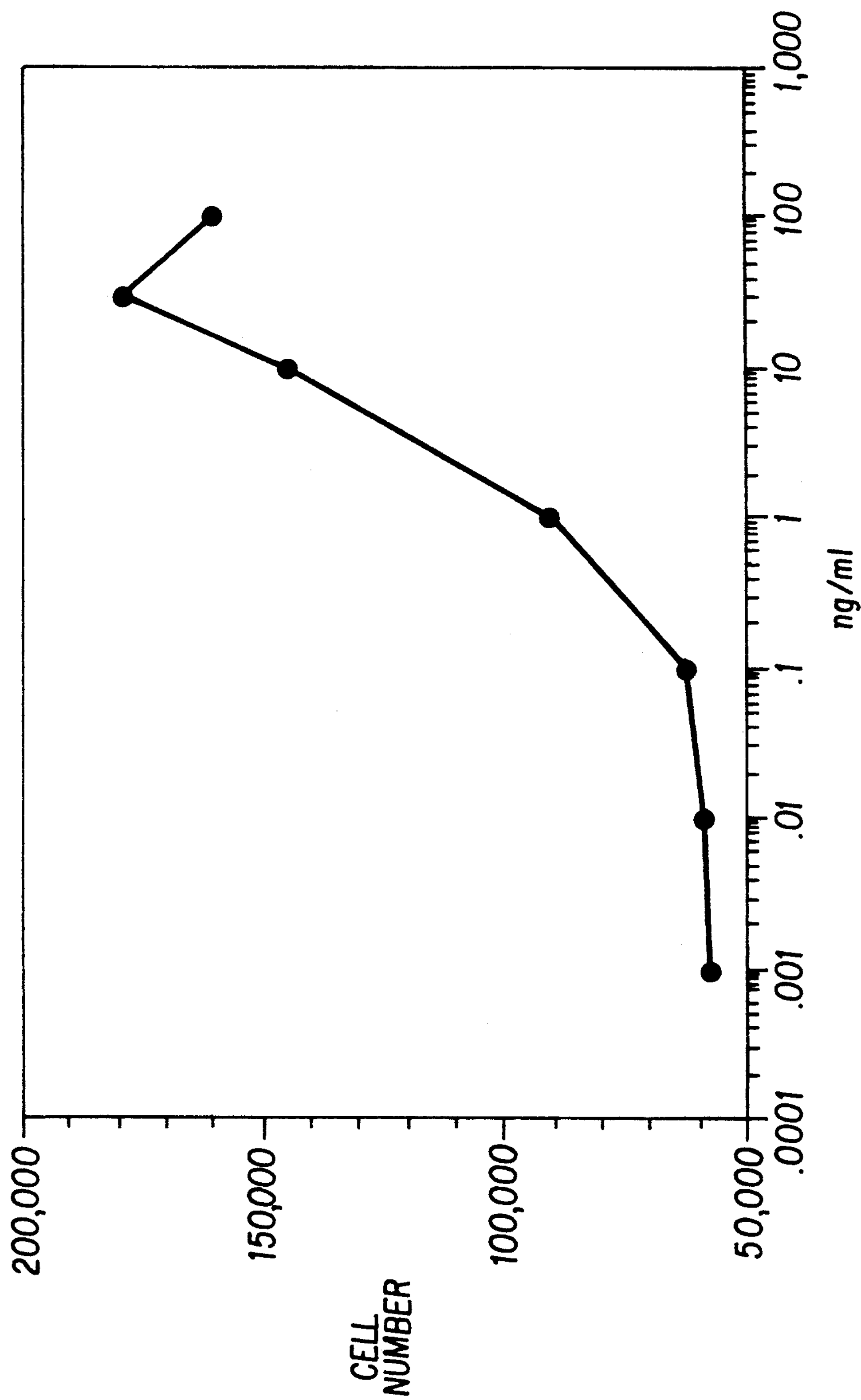

FIG. 2: The effect of the mixture of HBF-1 and HBF-2 eluted from heparin sepharose on the proliferation of bovine aortic arch endothelial cells Protein in the 3M NaCI eluate from heparin-Sepharose is determined by amino acids analysis and aliquots, after appropriate dilution in DMEM/BSA, are added to the cells for assay of mitogenic activity; Cell growth is assessed by cell counting, as described.

Figure 3:
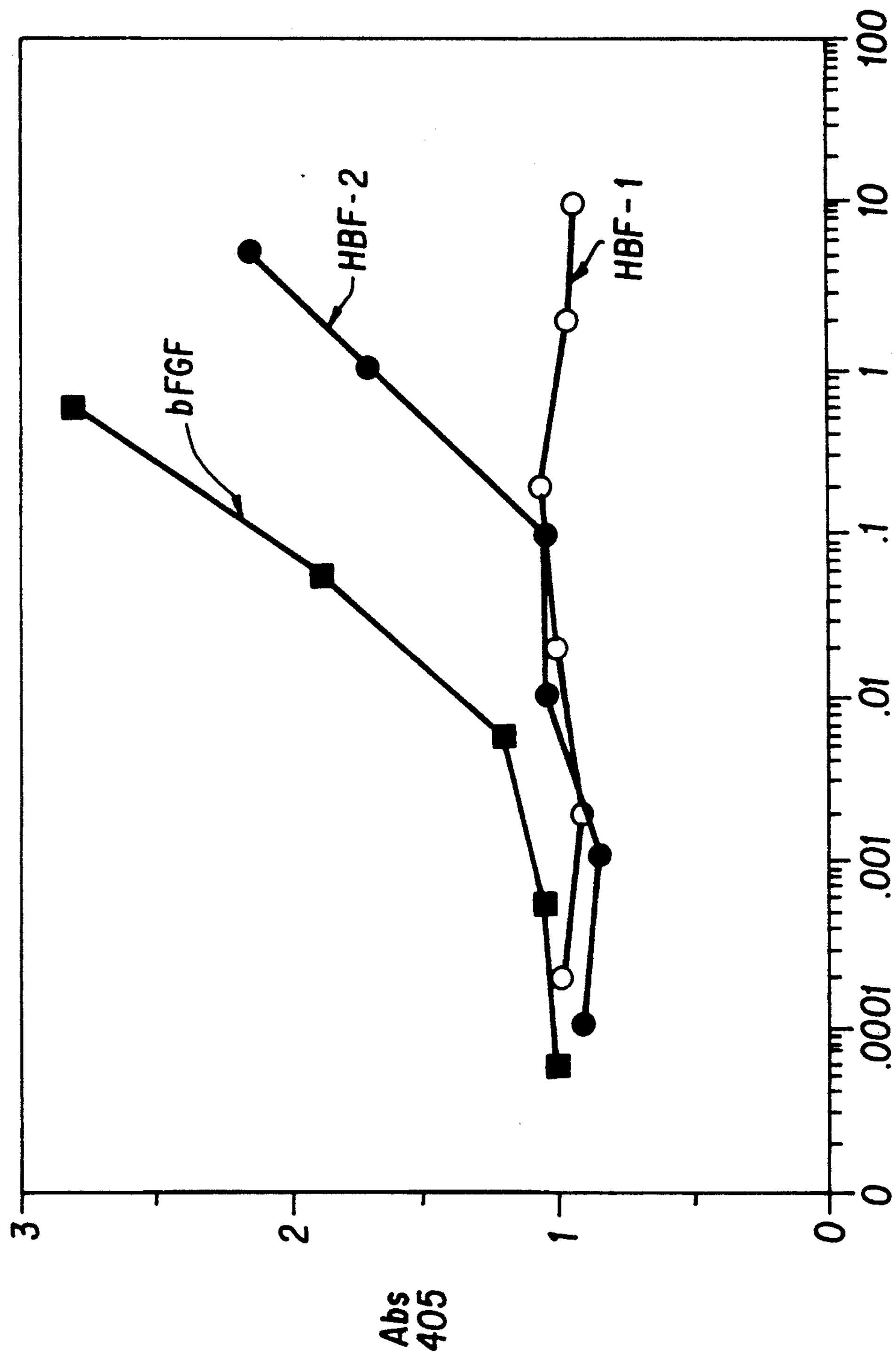

FIG. 3: The effect of RPLC purified HBF-1, HBF-2 and $glu^{3,5}$, $ser^{78,96}$bFGF on the proliferation of bovine aortic arch endothelial cells Samples of RPLC-purified mutant bFGF- -HBF-1 (-o-), HBF-2- -, appropriately diluted (in DMEM/-BSA), are added to cells, and growth is determined using the acid phosphatase assay.

SUMMARY OF THE INVENTION

The present invention relates to novel fragments of bFGF. The bFGF fragments are obtained by proteolytic degradation of the native bFGF or analogues thereof and result in fragments that are bound to heparin or heparin sepharose alone or in combination with other fragments of bFGF which bind to heparin or heparin sepharose. More specifically, the fragments of the present invention contain about amino acids 27 to 69 and about amino acids 70 to 155 of the native bFGF or analogues thereof which bind to heparin or which immobilize heparin or heparin sepharose. It has been unexpectedly found that the polypeptides of the present invention, those with about amino acids 70 to 155, exhibit a mitogenic activity much greater than peptides previously generated (34 and 35).

As such, it is an objective of the present invention to provide biologically active bFGF fragments, which bind, alone or in combination with other FGF fragments to heparin. Further, the fragment 70–155 also exhibits mitogenic activity. It is a further object of the invention to provide a method for generating said peptide fragments. Also, these fragments are useful in treating animals and patients to more quickly regenerate damaged and/or destroyed tissues as previously discussed. These and other objects of the present invention will become more apparent by the more detailed description of the invention provided hereinbelow.

DETAILED DESCRIPTION OF THE INVENTION

The present invention is exemplified by the following examples, which are illustrative and not limitative thereof.

EXAMPLE 1

Construction of Expression Plasmid

A synthetic gene encoding the 155 amino acid form of human basic FGF (26) cloned into pUC 18 was purchased from British Bio-technology, Oxford, UK. To facilitate manipulations, the internal NcoI restriction site, which includes the N-terminal methionine codon of the bFGF cDNA, is destroyed and replaced with a unique NdeI site. This is accomplished by excision of the nucleotide sequence (−12 to 36) with HindIII and BspMII and cloning of a synthetic fragment containing an internal NdeI site into pUC 18. The cDNA encoding bFGF is then excised from pUC 18 with NdeI and Bam HI and cloned into the NdeI and Bam HI sites of the expression vector pT7 Kan 5, a derivative of pET-3a containing the T7 promoter from RNA polymerase (38).

EXAMPLE 2

Construction of a Synthetic Gene Corresponding to the Human bFGF analog glu$^{3,5}$,ser$^{78\ 96}$bFGF In a first step, glu3,5-bFGF a chimeric FGF is constructed using a protocol that is identical to that described above for the introduction of the NdeI restriction site except that the codons for alanine and serine at positions 3 and 5, respectively, (a) are changed to encode glutamic acid (b);

5'AGCTTCATATGGCAGCCGGGAGCAT-CACCACGCTGCCCGCCCTT 3' (a)

5'AGCTTCATATGGCTGAAGGGGAAAT-CACCACGCTGCCCGCCCTT 3' (b)

Only the sense strands are shown for the original (a) and modified (b) fragments, respectively. The codons underlined indicate those changed to encode glutamic acid at positions 3 and 5.

The expression plasmid, pT7 glu$^{3,5}$-hbFGF, is then used as a template for oligonucleotide site-directed mutagenesis. Two mutagenic oligonucleotide primers are designed to change codons for cysteine at positions 78 and 96 to serine codons. The primer for serine at position 96 is to the sense strand (60-mer; 238–297) whereas that for serine at position 96 is to the antisense strand (30-mer; 251–222). In addition to these mutagenic primers, primers to the T7 promoter (nucleotide −12 to +13) and terminator regions (nucleotide −75 to −51) are designed (38). Mutation of the modified FGF gene is accomplished by use of the Polymerase Chain Reaction (PCR). Two reaction mixtures containing HindIII cut plasmid DNA are prepared; (i) T7 sense plus Ser 78 antisense primers to yield an expected 319 bp product, and (ii) T7 antisense plus Ser 96 sense primers to produce an expected 294 bp product. PCR mixtures are prepared according to standard instructions. PCR is performed using Taq polymerase for 30 amplification cycles each of 92° C. for 1 min, 50° C. for 5 sec, 72° C. for 1 min and the products analyzed by agarose gel electrophoresis. Excess primers are separated from the amplified DNA fragments by 3 successive rounds of concentration and dialysis using 30,000 MW cut-of microconcentrators (Millipore). Portions of the retentates are combined and amplified using the PCR as described above except that the primers used correspond to the T7 promoter (sense) and T7 terminator (antisense) regions. The 599 bp PCR product is then treated with NdeI and BamHI and purified by agarose gel electrophoresis. The purified fragment is then cloned into the T7 expression vector, pET-3a(M-13), a derivative of pET-3a.

EXAMPLE 3

Expression of glu$^{3,5}$,ser$^{78\ 96}$bFGF

Following sequence verification (39), the gene encoding the bFGF mutant is transformed into competent BL21 plys S cells. E. coli (E. coli strain that contains the lysozyme "s" plasmid) cells harboring the plasmid are grown in Luria broth containing ampicillin (100 μg/ml) and chloroamphenicol (34 μg/ml) at 37° C. to about 0.6 absorbance units at 600 nm, and bFGF synthesis is induced by addition of isopropyl-beta-thiogalactopyranoside (IPTG, 1 mM). The cells are then harvested 2 hours post induction by centrifugation at 4° C.

EXAMPLE 4

Purification of glu$^{3,5}$,ser$^{78\ 96}$bFGF.

Cell pellets from 1 liter-cultures are resuspended in 50 mM Tris, 0.1 mM EDTA buffer (pH 7.6; 30ml) and lysed by 3 rapid freeze/thaw cycles. The lysate is then treated with DNase 1 (20 μg/ml) in the presence of 5 mM MgC12 for 20 min at 4° C. and centrifuged to remove cell debris (10,000×g; 20 min). bFGF is purified from the supernatant solution by heparin sepharose affinity chromatography essentially as described (22) using a linear salt gradient from 0.6–3.0M NaCl. Fractions containing growth factor are pooled, diluted with Tris buffer (10 mM; pH 7.6) to give a final NaCl concentration of about 0.6 M and loaded onto a TSK Heparin-5PW column (0.75×7.5 cm; TosoHaas, Philadelphia, PA) equilibrated with 10 mM Tris, 0.6M NaCl (pH 7.6). Elution of bound material is monitored at 280 nm and is accomplished using a linear salt gradient (0.6–3.0 M NaCl in 60 min) at a flow rate of 0.7 ml/min.

Growth factor purified in this manner is analyzed for homogeneity by using reverse phase HPLC, monitoring elution at 210 nm, ($C_4$, Vydac; The Separations Group, Hesperia, CA) in an acetonitrile gradient (0–28% CH CN in 15 min; 28–60% CH3CN in 90 min) in 0.1% trifluoroacetic acid at a flow rate of 0.7 ml/min, N-terminal sequence analysis and sodium dodecyl sulfate polyacrylamide gel electrophoresis (SDS-PAGE) on 10–15% gradient and 20% homogeneous gels using a silver-stain detection system (Phastgel System, Pharmacia/LKB).

EXAMPLE 5

Proteolytic Digestion of glu$^{3,5}$, ser$^{78,96}$bFGF

A solution containing gl$^{3,5}$,ser$^{78,96}$bFGF (712 μg in 0.475 ml) is added to a drained slurry (0.2 ml) of heparin-Sepharose (Pharmacia/LKB, Uppsala, Sweden), previously equilibrated with Tris-HCl buffer (50 mM; pH 7.6), mixed and incubated at 4° C. After 60 min the supernatant solution is removed and the gel washed with 50 mM Tris-HCl pH 7.6 (0.4 ml). The gel slurry is resuspended in Tris-HCl buffer (0.2 ml), and pronase (Sigma Chemical Co.; Type XXV) is added to give a ratio of bFGF to pronase of 0.75:1.0 (w/w). The mixture is then incubated at 37° C. with agitation. After 24 hours the gel mixture is centrifuged, the supernatant solution removed and the drained gel washed with 10 mM Tris buffer (pH 7.6;3×0.4 ml) and Tris buffer containing 0.6 M NaCl L (2×0.4 ml) to remove non-specifically bound proteolytic products. Elution of bound material is effected by washing the heparin-Sepharose gel twice with Tris buffer containing 3M NaCl.

EXAMPLE 6

Analysis of Proteolytic Fragments of glu$^{3,5}$ser$^{78,96}$bFGF

Heparin-binding proteolytic fragments of bFGF are analyzed under reducing conditions on 20% polyacrylamide gels in the presence of sodium dodecyl sulfate (SDS-PAGE) using a silver-stain detection system (Phastgel System, Pharmacia/LKB). Peptide fragments are resolved by reverse phase HPLC ($C_4$, Vydac, Hesperia, CA) using an acetonitrile gradient in 0.1% trifluoroacetic acid at a flow rate of 0.7 ml/min. Elution of bound material is monitored at 210 nm. N-terminal sequence analyses of reverse phase purified peptides are performed on a model 477A pulsed-liquid phased sequence (Applied Biosystems, CA) equipped with an on-line PTH-derivative analyses (Model 120A, Applied Biosystems). Amino acid compositions are determined after HCl gas phase hydrolysis (5.7 M HCl 10.1% phenol; 24 hours at 110° C.) using a model 420A phenylisothiocyanate-derivatizer equipped with an on-line model 130A separation system (Applied Biosystems). Unless otherwise stated, procedures are performed according to the manufacturer's protocols.

Figure 1:
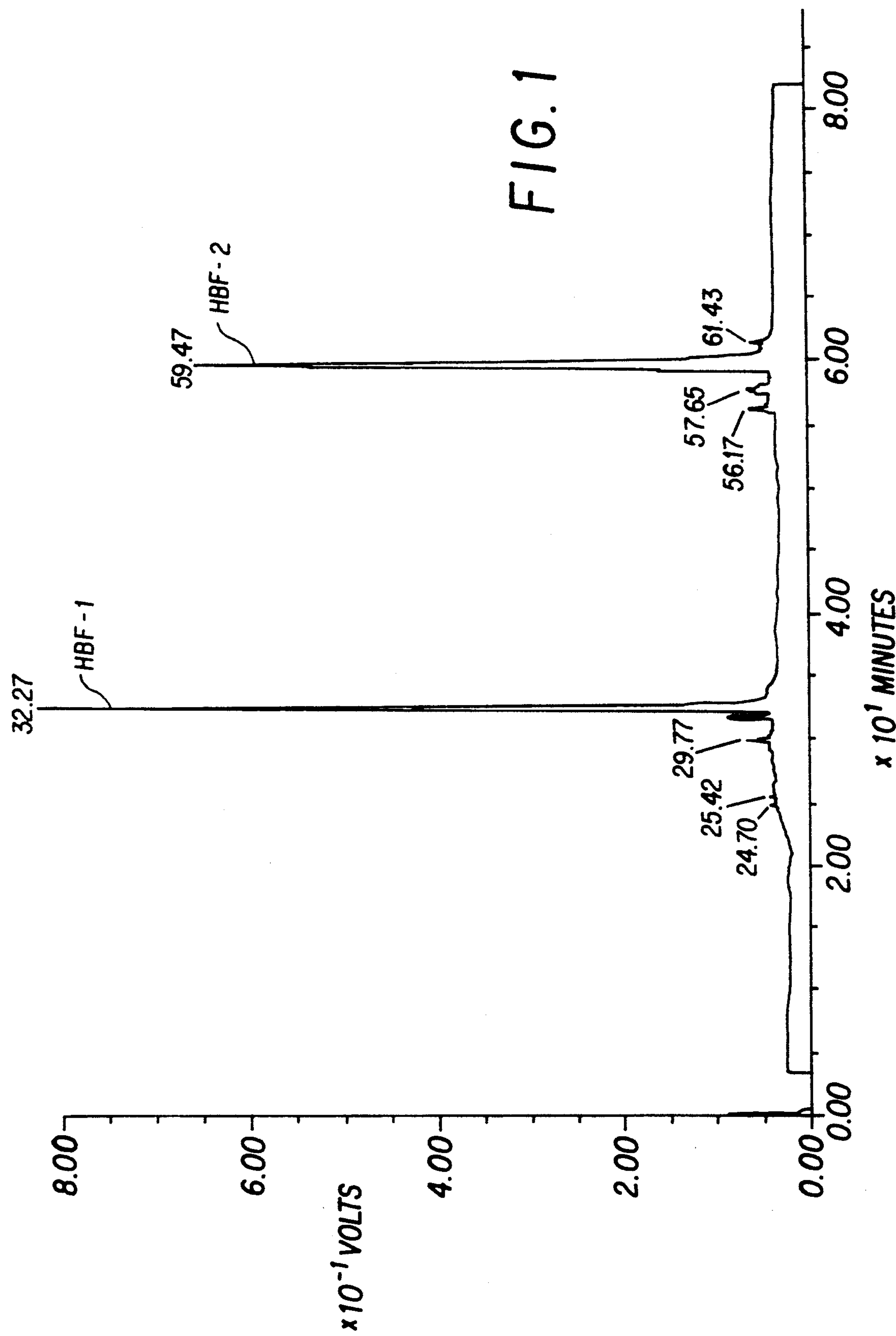
FIG. 1: RPLC purification of HBF-1 and HBF-2

Analysis by SDS-PAGE of heparin binding proteolytic fragments of hbFGF shows complete digestion of the 18kD band corresponding to glu$^{3,5}$,ser$^{78,96}$-bFGF and the generation of 2 lower molecular weight peptides that migrate as 11kD and 9kD species. RPLC of the growth factor digest eluted from heparin-Sepharose with 3M NaCl reveals 2 major peaks, termed heparin-binding fragment—1 and —2- (HBF-1 and HBF-2) (FIG. 1). The early eluting fragment, HBF-1, is identified by SDS-PAGE as the 9 kD species present in material eluted from heparin sepeharose, whereas, the more retarded fragment HBF-2 migrates in a position identical to that of the 11 kD fragment. N-terminal sequence analysis of the 2 RPLC-purified fragments gives single sequences consistent with peptide regions that begin at residue 27 and residue 70 of glu$^{3,5}$,ser$^{78}$ $^{96}$bFGF for HBF-1 and HBF-2, respectively.

These sequences also are shown as Sequence ID No. 1 and 3, respectively. Sequence I.D. No. 2 shows the sequence of the wild-type fragment corresponding to amino acids 70 to 155. The amino acid compositions of HBF-1 and BF-2 (Table 1) correspond, within experimental error, to glu$^{3,5}$ser$^{78,96}$-bFGF sequence regions of residues 27–69 and 70–155 respectively.

TABLE 1

| MOL OF AMINO ACID/MOL OF PEPTIDE | | | | |
|---|---|---|---|---|
| | HBF-1 | | HBF-2 | |
| Amino acid | Found | Theory | Found | Theory |
| Asx | 4.87 | 5 | 6.04 | 6 |
| Glx | 5.02 | 5 | 5.76 | 6 |
| Ser | 1.23 | 1 | 7.56 | 10 |
| Gly | 4.44 | 4 | 7.64 | 7 |
| His | 2.15 | 2 | 0.00 | 0 |
| Arg | 5.01 | 5 | 6.79 | 6 |
| Thr | 0.00 | 0 | 5.71 | 5 |
| Ala | 0.99 | 1 | 6.16 | 6 |

TABLE 1-continued

| MOL OF AMINO ACID/MOL OF PEPTIDE | | | | |
|---|---|---|---|---|
| | HBF-1 | | HBF-2 | |
| Amino acid | Found | Theory | Found | Theory |
| Pro | 2.99 | 3 | 2.38 | 2 |
| Tyr | 1.00 | 1 | 5.82 | 6 |
| Val | 2.07 | 2 | 4.84 | 5 |
| Met | 0.00 | 0 | 1.86 | 2 |
| Cys | N.D. | 1 | N.D. | 1 |
| Ile | 1.87 | 2 | 2.43 | 2 |
| Leu | 3.93 | 4 | 8.38 | 8 |
| Phe | 2.28 | 2 | 4.30 | 4 |
| Trp | N.D. | 0 | N.D. | 1 |
| Lys | 4.73 | 5 | 8.32 | 9 |
| Total | | 43 | | 86 |

Amino acid compositions of HBF-1 and HBF-2 Amino acid analyses of HBF-1 (45 pmol) and HBF-2 (25 pmol) are performed in triplicate. Relative standard deviations are less than 10%. (N.D., not determined).

EXAMPLE 7

BIOASSAY

Reverse phase HPLC-purified samples are immediately diluted (1:5) in Dulbecco's modified Eagle's medium (DMEM) containing 1% bovine serum albumin (BSA). Mitogenic activities of bFGF and bFGF peptide fragments are determined using bovine vascular endothelial cells derived from adult aortic arch as described (22). Briefly, cells are seeded at an initial density of $0.8\times10^4$ cells per 24 well plate in 0.5 ml DMEM/10% calf serum (Hyclone, Logan, UT), penicillin (100 units/ml), streptomycin (100 μg/ml), and L-glutamine (2 mM). Two hours after plating, 20 μl aliquots of appropriate dilutions of bFGF in DMEM containing 0.5% BSA are added. After 5 days in culture, duplicate plates are trysinized and cell densities determined by cell counting in a Coulter counter. Alternatively, growth curves in the presence and absence of bFGF are determined by measuring acid phosphatase levels after cell lysis (40). Cells are seeded at an initial cell density of 1000–1200 cells per well (0.32 $cm^2$ flat bottom 96-well plates) in 0.25 ml DMEM/10% calf serum containing antibiotics and L-glutamine (see above). After plating of cells, 10 μl-aliquots of appropriate dilutions of growth factor and peptide fragments in DMEM/0.5% BSA are added. After 4–5 days, cell growth is assessed in each well by measuring acid phosphatase levels after cell lysis using p-nitrophenyl phosphate as substrate (40). The absorbance at 405 nm for each sample is determined using UV max kinetic microplate reader (Molecular Devices). Determinations are made in triplicate. No significant differences are observed in the shape of dose response curves or in concentrations of bFGF required for half maximal and maximal stimulation of cell growth when cell growth is determined by either method.

EXAMPLE 8

The 3M NaCl eluate from heparin-Sepharose containing an approximately equimolar mixture of HBF-1 and HBF-2 is examined for mitogenic activity. The mixture induces a dose-dependent proliferation of bovine endothelial cells, with the dose for half-maximal growth stimulation being approximately 10 fold higher as compared to intact bFGF (FIG. 2). In order to determine the mitogenic properties of each component, an attempt to resolve the 2 mutant FGF fragments is made. Unexpectedly, the chromatographic behaviors of HBF-1 and HBF-2, on Mono-S cation exchange and TSK heparin HPLC under a variety of conditions, are identical to those of intact bFGF and give no resolution of HBF-1 and HBF-2. However, since RPLC affords effective separation of the 2 components (FIG. 1) the mitogenic properties of RPLC-purified HBF-1 and HBF-2 are compared to those of RPLC-purified bFGF. These conditions are known to reduce the mitogenic activity of bFGF by 10-20 fold, presumably as a consequence of protein denaturation. In the present experiment RPLC-purified bFGF is 1/10th as active as intact bFGF. RPLC-purified HBF-1 does not appear to affect cell growth, whereas HBF-2 exhibits a dose-dependent stimulatory response (FIG. 3) with a potency that is 25-50 fold lower than that of RPLC-purified glu$^{3,5}$,ser-$^{78,96}$-bFGF ($ED_{50}$ of RPLC-purified HBF-2 and glu$^{3,5}$-,ser$^{78,96}$-bFGF are about 3 and 0.1 pmol/ml, respectively). Assuming that the mitogenic activity of HBF-2 is reduced by the same degree as bFGF under RPLC-conditions, then an $ED_{50}$ of about 150-300 fmol/ml may be predicted for native HBF-2. This estimate is consistent with an $ED_{50}$ of about 150 fmol/ml obtained from the data presented in FIG. 2 for the mixture containing HBF-1 and HBF-2 eluted from heparin-Sepharose. In our assay, the potency of intact bFGF or glu$^{3,5}$,ser$^{78,96}$-bFGF is approximately 17 fmol/ml Thus HBF-2 with an intact conformation is about 10 fold less potent than intact bFGF.

TABLE 2

| PEPTIDE | MASS | MITOGENIC ACTIVITY | REF |
|---|---|---|---|
| bFGF(2-155) | 17.2 | 1.00 | (14) |
| bFGF(10-155) | 16.4 | 1.00 | (35) |
| bFGF(23-155) | 15.2 | 0.68 | (35) |
| bFGF(50-155) | 12.1 | 0.02 | (35) |
| bFGF(70-155) | 9.5 | 0.04-0.02 | HBF-2 |
| bFGF(112-155) | 5.0 | $10^{-5}$-$10^{-6}$ | (34) |
| bFGF(33-77) | 5.0 | $10^{-5}$-$10^{-6}$ | (34) |
| bFGF(109-129) | 2.7 | $10^{-5}$-$10^{-6}$ | (34) |

Relative mitogenic activities of bFGF peptide fragments

Mitogenic activities for each peptide are estimated from published data as indicated and are expressed relative to the $ED_{50}$ values for bFGF(2-155) or bFGF(10-155). Relative mitogenic potencies quoted from (34) are estimated from incomplete data. Values reported for HBF-2 are relative to the $ED_{50}$ values determined for RPLC purified bFGF. Similar values may be obtained by comparison of the $ED_{50}$ value for bFGF to that of the mixture containing HBF-1 and HBF-2 eluted from heparin sepharose (see text).

The DNA sequences, plasmids and/or microorganisms deposited in connection with the present patent application, except where specified to the contrary, are deposited in American Cyanamid Company's culture collection maintained in Pearl River, New york and are available to the public when legally appropriate to do so. Further, the following are deposited additionally with the American Type Culture Collection (ATCC) in Rockville, Maryland 20952, U.S.A. on the date indicated with the ATCC accession numbers indicated:

BL21 lysS/pET glu$^{3,5}$ser$^{78,96}$ deposited on Nov. 13, 1990 with ATCC No. 68478.

BL21 lys-S/pET glu$^{3,5}$hbFGF deposited on Nov. 13, 1990 with ATCC No. 68477.

The above two contain the DNA of glu$^{3,5}$ser$^{78,96}$ hbFGF and glu$^{3,5}$hbFGF as described herein.

BIBLIOGRAPHY

1. Baird, A. and Bohlen, P. (1990) in "Peptide Growth Factors and their Receptors" (Sporn, M. and Roberts, A., Eds) Handbook of Exp. Pharmacol. 95(1), pp369–418, Springer.

2. Gospodarowicz, D., Nature 249:123–127 (1974).

3. Burgess, W. H. and Maciag, T., Ann Rev. Biochem 8:575-606 (1989).

4. Gospodarowicz D., et al., Nat. Cancer Insti. Mon. 48:109–130 (1978).

5. Davidson, J. M., et al., J. Cell Bio.100: 1219–1227 (1985).

6. U. Franco, W. P., U.S. Pat. No. 4,296,100 (1981).

7. U. Franco, W. P., U.S. Pat. No. 4,378,347 (1983)

8. Walicke, P., Et al., Proc. Nat. Acac. Sci. USA 83: 3012–3016 (1986)

9. Esch, F., et al., Proc. Nat. Acad. Sci USA 82: 6507–6511 (1985)

10. Gospodarowicz, D. et al., U.S. Pat. No. 4,785,079 (1988).

11. Gospodarowicz, D. et al, U.S. Pat. No. 4,902782 (1990).

12. Iwane, M., et al., Biochem. Biophys. Res. Commun. 146:470–477 (1987).

13. Squires, C. H., et al., J. Biol. Chem. 263: 16297–16302 (1988).

14. Barr, P. J., et al., Biol. Chem. 263:16471–16478 (1988).

15. Esch., F., et al., Eur. pat. Appl. Pub. 281,822 (1988).

16. Seno, M., et al., Eur. Pat. Appl. Pub. 281,822 (1988).

17. Arakawa, T. and Fox, G. M., Eur. Pat. Appl. Pub. 320,148.

18. Thomas and Linemeyer, Eur. Pat. Appl. Pub. 319,052 (1989).

19. Seno, M., et al., Eur. Pat Appl. Pub. 326,907 (1989).

20. Fiddes, J. C., et al., Eur. Pat. Appl. Pub. 298,723 (1989).

21. Bergonzoni, L., et al., Eur. Pat Appl. Pub. 363,675 (1989)

22. Gospodarowicz, D., Cheng, J., Lui, G., Baird, A., and Bohlen, P. (1984) Proc. Natl. Acad. Sci. 6963–6967.

23. Gospodarowicz. D. and Cheng, J. (1986) J. Cell. Physiol. 128, 475–484.

24. Sommer, A. and Rifkin, D. B. (1989) J. Cell. Physiol. 138, 215–220.

25. Damon, D. H. Lobb, R. R., D'Amore, P. A., and Wagner, J. A. (1989) J. Cell. Physiol 138, 221–226.

26. Abraham, J. A., Whang, J. L., Tumolo, A., Mergia, A., Friedman, J., Gospodarowicz. D., and Fiddes, J. C. (1986) EMBO J. 5, 2523–2528.

27. Vlodavsky, I., Folkman, J., Sullivan, R., Fridman, R., Ishai-Michaeli, R., Sasse, J., and Klagsbrun, M. (1987) Proc. Natl. Acad. Sci. 84, 2292–2296.

28. Folkman, J., Klagsbrun, M., Sasse, J., Wadzinski, M. Ingber, D., and Vlodavsky, 1. (1988) Am. J. Pathol. 130, 393–400.

29. Bashkin, P., Doctrow, S., Klagsbrun, M. Svahn, C. M., Folkman, J., and Vlodavsky, I. (1989) Biochemistry 28, 1737–1743.

30. Presta, M., Maier, J. A. M. Rusnati, M., and Ragnotti, G. (1989) J. Cell. Physiol. 140 68–74.

31. Saksela, O. and Rifkin, D. B. (1990) J. Cell. Biol. 110, 767–775.

32. Vlodavsky, I., Michaeli, R. I., Bar-Ner, M., Fridman, R., Horowitz. A. T. Fuks, Z. and Biran, S. (1988) Israeli J. Med. Sci 24, 464–470.

33. Nakajima, M., Irimura, T. and Nicolson, G. L. (1988) J. Cell Biochem. 36, 157–167.

34. Baird, A., Schubert, D., Ling, N. and Guillemin, R. (1988) Proc. Natl. Acad. Sci. 85, 2324–2328.

35. Seno, M., Sasada, R. KuroKawa, T. and Igarashi, K. (1990) Eur. J. Biochem. 188, 239–245.

36. Fox G. M., Schiffer, S. G., Rohde, M. F., Tsai, L. B. Banks, A. L. and Arakawa, T., (1988) J. Biol. Chem 263, 18452–18458.

37. Andrews, P. C. and Dixon, J. E., (1987) Anal. Biochem. 161, 525.

38. Rosenberg, A. H., Lade, B. N., Chui, D., Dunn, J. J. and Studier, F. W., (1987) Gene 56, 125–135.

39. Sanger, F., Nicklen, S., and Coulson, A. R. (1977) Proc. Natl. Acad. Sci. 74, 5463–5467.

40. Connolly, D. T., Knight, M. B. Harakas, N. K. Wittwer, A. J. and Feder, J., (1986) Anal. Biochem 152, 136–140.

What is claimed is:

1. An isolated DNA molecule consisting of a sequence that codes for a fragment of mammalian recombinant basic fibroblast growth factor, the fragment consisting of amino acids 70 to 155 of basic fibroblast growth factor.

2. An isolated DNA molecule consisting of a sequence that codes for a fragment of mammalian recombinant basic fibroblast growth factor, the fragment consisting of amino acids 70 to 155 of mammalian basic fibroblast growth factor, the sequence modified by replacing amino acid 78 and amino acid 96 independently with an amino acid selected from the group consisting of alanine, glycine, arginine, tryptophan, lysine, aspartic acid, glutamic acid, asparagine, glutamine, histidine, isoleucine, leucine, valine, phenylalanine, tyrosine, methionine, serine, threonine and proline.

3. A DNA sequence of claim 2, wherein the sequence coding for the amino acids at positions 78 and 96 are a DNA sequence coding for serine.

* * * * *